(12) United States Patent
Yin et al.

(10) Patent No.: US 11,983,844 B2
(45) Date of Patent: May 14, 2024

(54) PANORAMIC STITCHING METHOD, APPARATUS, AND STORAGE MEDIUM

(71) Applicant: Chison Medical Technologies Co., LTD., Wuxi (CN)

(72) Inventors: Chen Yin, Wuxi (CN); Mingchang Zhao, Wuxi (CN); Ruoli Mo, Wuxi (CN)

(73) Assignee: CHISON MEDICAL TECHNOLOGIES CO. LTD., Wuxi (CN)

( * ) Notice: Subject to any disclaimer, the term of this patent is extended or adjusted under 35 U.S.C. 154(b) by 20 days.

(21) Appl. No.: 17/420,762

(22) PCT Filed: Dec. 31, 2019

(86) PCT No.: PCT/CN2019/130603
§ 371 (c)(1),
(2) Date: Jul. 6, 2021

(87) PCT Pub. No.: WO2021/134506
PCT Pub. Date: Jul. 8, 2021

(65) Prior Publication Data
US 2022/0343460 A1    Oct. 27, 2022

(51) Int. Cl.
*G06T 3/00* (2006.01)
*G06T 3/40* (2006.01)
(Continued)

(52) U.S. Cl.
CPC .......... *G06T 3/4038* (2013.01); *G06T 3/0056* (2013.01); *G06T 3/4046* (2013.01)

(58) Field of Classification Search
CPC ... G06T 3/4038; G06T 3/0056; G06T 3/4046; G06T 3/0075; A61B 5/067;
(Continued)

(56) References Cited

U.S. PATENT DOCUMENTS

| 2017/0150235 A1 | 5/2017 | Mei et al. |
| 2020/0196984 A1* | 6/2020 | Sprung .................... G06T 7/10 |
| 2021/0183012 A1* | 6/2021 | Matsumoto .......... H04N 23/698 |

FOREIGN PATENT DOCUMENTS

| CN | 105447850 A | 3/2016 |
| CN | 105447850 A | 3/2016 |

(Continued)

OTHER PUBLICATIONS

International Search Report for PCT/CN2019/130603, dated Sep. 30, 2020.
(Continued)

*Primary Examiner* — Siamak Harandi
(74) *Attorney, Agent, or Firm* — Finnegan, Henderson, Farabow, Garrett & Dunner

(57) ABSTRACT

The present disclosure discloses a panoramic stitching method, an apparatus, and a storage medium. A transformation matrix obtaining method includes: obtaining motion data detected by sensors, wherein the sensors are disposed on a probe used to collect images, and the motion data is used to represent a moving trend of the probe during image collection; inputting the motion data into a pre-trained neural network, to calculate matrix parameters by using the neural network; calculating a transformation matrix by using the matrix parameters, wherein the transformation matrix is used to stitch images collected by the probe, to obtain a panoramic image. In the present disclosure, the transformation matrix can be calculated and the images can be stitched without using characteristics of the images, and factors such as brightness and the characteristics of the images do not impose an impact, thereby improving transformation matrix calculation accuracy, and improving an image stitching effect.

20 Claims, 8 Drawing Sheets

(51) Int. Cl.
*G06T 3/4038* (2024.01)
*G06T 3/4046* (2024.01)

(58) Field of Classification Search
CPC . A61B 2576/00; A61B 8/4254; A61B 8/5253; A61B 2034/2048; G06N 3/045; G06N 3/048; G06N 3/08
See application file for complete search history.

(56) References Cited

FOREIGN PATENT DOCUMENTS

| | | |
|---|---|---|
| CN | 106920215 A | 7/2017 |
| CN | 106920215 A | 7/2017 |
| CN | 109584283 A | 4/2019 |
| CN | 109584283 A | 4/2019 |
| CN | 109740753 A | 5/2019 |
| CN | 109740753 A | 5/2019 |
| CN | 110288653 A | 9/2019 |
| CN | 110288653 A | 9/2019 |

OTHER PUBLICATIONS

International Search Report for PCT/CN2019/130603 dated Sep. 24, 2020.

* cited by examiner

PANORAMIC STITCHING METHOD, APPARATUS, AND STORAGE MEDIUM

This application is a national stage filing under 35 U.S.C. § 371 of International Application No. PCT/CN2019/130603, filed Dec. 31, 2019, which is incorporated herein by reference in its entirety.

TECHNICAL FIELD

The present disclosure relates to the field of image stitching technologies, and specifically, to a panoramic stitching method, an apparatus, and a storage medium.

BACKGROUND

An image stitching technology is a technology of stitching several overlapping images into one seamless panoramic or high-resolution image. During image collection, an entire image of a complete area of interest cannot be seen in one image due to factors such as different times and different angles. For example, a divergence range of ultrasonic sound waves emitted by a conventional ultrasonic probe is limited, and a size of the probe is also fixed. As a result, only ultrasonic images in specified ranges can be generated, and an entire image of an area of interest cannot be generated. In an application process in the medical field, doctors can form an entire image of the area in the brain only based on memory and with reference to their experience, to observe statuses of adjacent tissues. Consequently, rapidity and accuracy of medical diagnosis are affected to some extent.

For the foregoing problem, there have been related studies in which images collected by an ultrasonic probe in a moving process are stitched into one panoramic image by using a conventional registration technology of adjacent images, to show a structure of an entire tissue on one image, thereby facilitating the diagnosis of a doctor.

However, accuracy of a panoramic image obtained by the foregoing panoramic stitching method is low, and when the ultrasonic probe is provided with an electromagnetic positioning system, the foregoing method for implementing panoramic stitching has high system costs and expensive architecture.

SUMMARY

To solve the technical problem in the prior art that panoramic image stitching accuracy is low, the present disclosure provides a transformation matrix obtaining method, a panoramic image stitching method, a neural network training method, an apparatus, a device, and a storage medium.

A first aspect of the present disclosure provides a transformation matrix obtaining method, including the following steps: obtaining motion data detected by sensors, wherein the sensors are disposed on a probe used to collect images, and the motion data is used to represent a moving trend of the probe during image collection; inputting the motion data into a pre-trained neural network, and calculating matrix parameters by using the neural network; and calculating a transformation matrix by using the matrix parameters, wherein the transformation matrix is used to stitch the images collected by the probe, to obtain a panoramic image.

Optionally, the neural network includes a convolutional neural network, a recursive neural network, and a fully connected network. The step of inputting the motion data into a pre-trained neural network, and calculating matrix parameters by using the neural network includes: performing convolution calculation on the motion data by using the convolutional neural network, to obtain a data feature of the motion data as an output of the convolutional neural network; performing, by using the recursive neural network, recursive operation on the data feature output by the convolutional neural network, to obtain a recursive calculation result as an output of the recursive neural network; and performing, by using the fully connected network, regression calculation on the recursive calculation result output by the recursive neural network, to obtain the matrix parameters.

Optionally, there are multiple sensors, the convolutional neural network includes a first convolutional neural network and multiple second convolutional neural networks in one-to-one correspondence to the multiple sensors, and an input of the first convolutional neural network is connected to outputs of the multiple second convolutional neural networks.

Optionally, the sensors include an accelerometer and a gyroscope.

Optionally, the step of performing convolution calculation on the motion data by using the convolutional neural network, to obtain a data feature of the motion data includes: performing, by using the second convolutional neural networks, convolution processing on the motion data detected by the sensors corresponding to the second convolutional neural networks; and merging outputs of the multiple second convolutional neural networks and performing convolution processing by using the first convolutional neural network, to obtain the data feature.

Optionally, the step of merging outputs of the multiple second convolutional neural networks and performing convolution processing by using the first convolutional neural network, to obtain the data feature includes: tiling data output by each second convolutional neural network into one-dimensional data; and superposing one-dimensional data corresponding to all of the second convolutional neural networks, and performing deep convolution calculation on the superposed data by using the first convolutional neural network, to obtain the data feature.

Optionally, the step of obtaining motion data detected by sensors includes: obtaining detection data, of to-be-detected duration, detected by each sensor; and equally dividing each piece of detection data into multiple segments of data according to a dimension of the to-be-detected duration; and performing Fourier transform on the multiple segments of data corresponding to each sensor to obtain the motion data.

A second aspect of the present disclosure provides a panoramic image stitching method, including the following steps: detecting multiple consecutive images of a target area by using a probe; obtaining a transformation matrix between adjacent images in the multiple images by using the transformation matrix acquisition method described in the first aspect; and stitching the multiple images based on the obtained transformation matrix to obtain a panoramic image.

A third aspect of the present disclosure provides a neural network training method, including the following steps: obtaining training sample data, wherein the sample data includes motion data detected by sensors and matrix parameters corresponding to the motion data, the sensors are disposed on a probe used to collect images, the motion data is used to represent a moving trend of the probe during image collection, and the matrix parameters are parameters in a transformation matrix used to obtain a panoramic image through stitching; and training a pre-established neural network model by using the training sample data, to obtain a neural network used to obtain the transformation matrix.

Optionally, the step of obtaining training sample data includes: obtaining body membrane images collected by the probe; determining a transformation matrix of two adjacent body membrane images by using coordinates of target sites disposed on the adjacent body membrane images; calculating matrix parameters of the transformation matrix by using a least square method; and obtaining the motion data detected by the sensors, and using the matrix parameters and the motion data as the training sample data.

A fourth aspect of the present disclosure provides a transformation matrix obtaining apparatus, including: a motion data obtaining module, configured to obtain motion data detected by sensors, wherein the sensors are disposed on a probe used to collect images, and the motion data is used to represent a moving trend of the probe during image collection; a parameter calculation module, configured to input the motion data into a pre-trained neural network, and calculate matrix parameters by using the neural network; and a matrix calculation module, configured to calculate a transformation matrix by using the matrix parameters, wherein the transformation matrix is used to stitch the images collected by the probe, to obtain a panoramic image.

A fifth aspect of the present disclosure provides a panoramic image stitching apparatus, including: a detection module, configured to detect multiple consecutive images of a target area by using a probe; the transformation matrix obtaining apparatus described in the fourth aspect, configured to obtain a transformation matrix between adjacent images in the multiple images; and a stitching module, configured to stitch the multiple images based on the obtained transformation matrix, to obtain a panoramic image.

A sixth aspect of the present disclosure provides a neural network training apparatus, including: a sample obtaining module, configured to obtain training sample data, wherein the sample data includes motion data detected by sensors and matrix parameters corresponding to the motion data, the sensors are disposed on a probe used to collect images, the motion data is used to represent a moving trend of the probe during image collection, and the matrix parameters are parameters in a transformation matrix used to obtain a panoramic image through stitching; and a training module, configured to train a pre-established neural network model by using the training sample data, to obtain a neural network used to obtain the transformation matrix.

A seventh aspect of the present disclosure provides a computer apparatus, including a memory, a processor, and a computer program that is stored in the memory and that can be run on the processor. When executing the computer program, the processor implements the steps of any method described above.

An eighth aspect of the present disclosure provides a computer-readable storage medium, storing a computer program. When the computer program is executed by a processor, the steps of any method described above are implemented.

According to the embodiments of the present disclosure, the motion data of the probe during image collection is obtained, the motion data is calculated and analyzed by using the pre-trained neural network, to obtain a moving change of the probe, and then the transformation matrix of the images is calculated. To be specific, an image change is calculated indirectly, the transformation matrix can be calculated and the images are stitched without using features of the images, and factors such as brightness and features of the images do not impose any impact, thereby improving transformation matrix calculation accuracy, and improving an image stitching effect. In addition, the motion data is obtained by using the sensors in the probe and an electromagnetic positioning system does not need to be added, thereby improving panoramic stitching accuracy and reducing system costs.

BRIEF DESCRIPTION OF THE DRAWINGS

To describe the technical solutions in the specific embodiments of the present disclosure or in the prior art more clearly, the following briefly describes the accompanying drawings required for describing the specific embodiments or the prior art. Apparently, the accompanying drawings in the following description show merely some embodiments of the present disclosure, and a person of ordinary skill in the art may derive other drawings from these accompanying drawings without creative efforts.

DETAILED DESCRIPTION

The following clearly and completely describes the technical solutions in the embodiments of the present disclosure with reference to the accompanying drawings in the embodiments of the present disclosure. Apparently, the described embodiments are some but not all of the embodiments of the present disclosure. All other examples obtained by a person of ordinary skill in the art based on the embodiments of the present disclosure without creative efforts shall fall within the protection scope of the present disclosure.

In the descriptions of the present disclosure, terms such as "first", "second", and "third" are merely for the purpose of description, but cannot be understood as indicating or implying relative importance.

In addition, the technical features in different embodiments of the present disclosure described below can be combined provided that there is no conflict therebetween.

Embodiment 1

Figure 1:
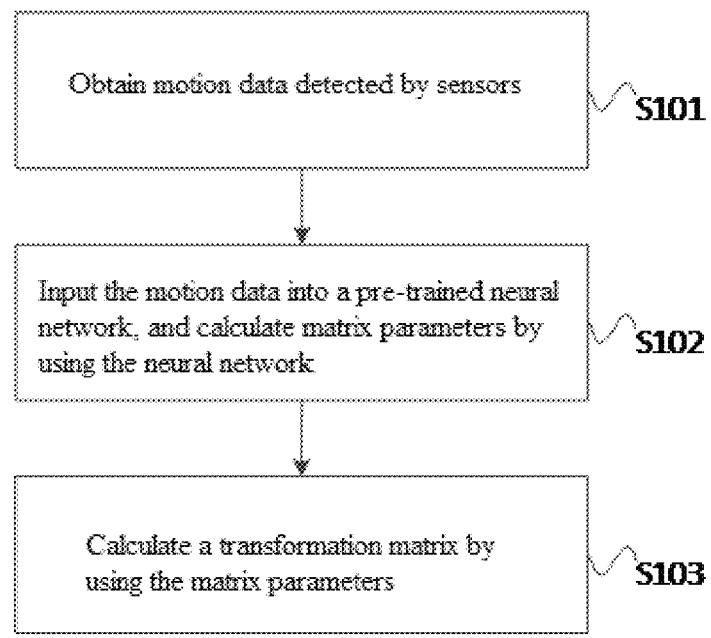
FIG. 1 is a flowchart of a specific example of a transformation matrix obtaining method according to Embodiment 1 of the present disclosure.

This embodiment of the present disclosure discloses a transformation matrix obtaining method. The method is mainly used to obtain a transformation matrix used for image stitching. Specifically, it is mainly applicable to a technology of stitching images collected by a probe provided with sensors. As shown in FIG. 1, the method includes the following steps:

Step S101: motion data detected by the sensors is obtained, wherein the sensors are disposed on the probe used to collect images, and the motion data is used to represent a moving trend of the probe during image collection.

The sensors may be an accelerometer and a gyroscope. The accelerometer is used to detect acceleration of the probe when the probe is moved to collect images, and the gyroscope is used to detect angle changes of the probe in three directions when the probe is moved to collect images. Specifically, the acceleration sensor reflects movement changes in three directions of x, y, and z, and the gyroscope can calculate angle changes. These variations can reflect a relative moving trend of the probe to some extent, and can quantify a moving position and a moving angle of the probe, to calculate a change pattern between images scanned by the probe.

The probe in this embodiment of the present disclosure may be an image collection apparatus provided with the sensors used to collect motion data, including, but not limited to, an ultrasonic probe, and a specific form and structure of the probe are not limited.

Step S102: the motion data is input into a pre-trained neural network, and matrix parameters are calculated by using the neural network.

Step S103: a transformation matrix is calculated by using the matrix parameters, wherein the transformation matrix is used to stitch the images collected by the probe, to obtain a panoramic image.

In this embodiment of the present disclosure, the neural network is a neural network pre-trained by using the motion data and the corresponding matrix parameters as a training sample. After the training (a process of training the neural network in this embodiment of the present disclosure will be described later), the neural network has a capability of identifying a relationship between the motion data and the matrix parameters. Therefore, after the motion data collected by the sensors is obtained, the corresponding matrix parameters can be calculated and determined by using the neural network, to calculate the transformation matrix by using the matrix parameters.

For example, a to-be-obtained transformation matrix is as follows:

$$M = \begin{vmatrix} a & b & c \\ d & e & f \\ 0 & 0 & 1 \end{vmatrix},$$

wherein matrix parameters involved include a, b, c, d, e, and f.

After the motion data collected by the sensors is input into the neural network for learning and training, the foregoing parameters a, b, c, d, e, and f can be calculated by using the neural network, to obtain the transformation matrix used to obtain the panoramic image through stitching.

According to this embodiment of the present disclosure, the motion data of the images collected by the probe is obtained, and the motion data is calculated and analyzed by using the pre-trained neural network, to obtain a moving change of the probe, and calculate the transformation matrix of the images. To be specific, an image change is calculated indirectly. The transformation matrix can be calculated and the images can be stitched without using features of the images. Therefore, factors such as brightness and features of the images do not impose any impact, thereby improving transformation matrix calculation accuracy, and improving an image stitching effect. In addition, the motion data is obtained by using the sensors in the probe and the transformation matrix is accurately calculated without adding an electromagnetic positioning system, thereby improving panoramic stitching accuracy and reducing system costs.

Figure 2:
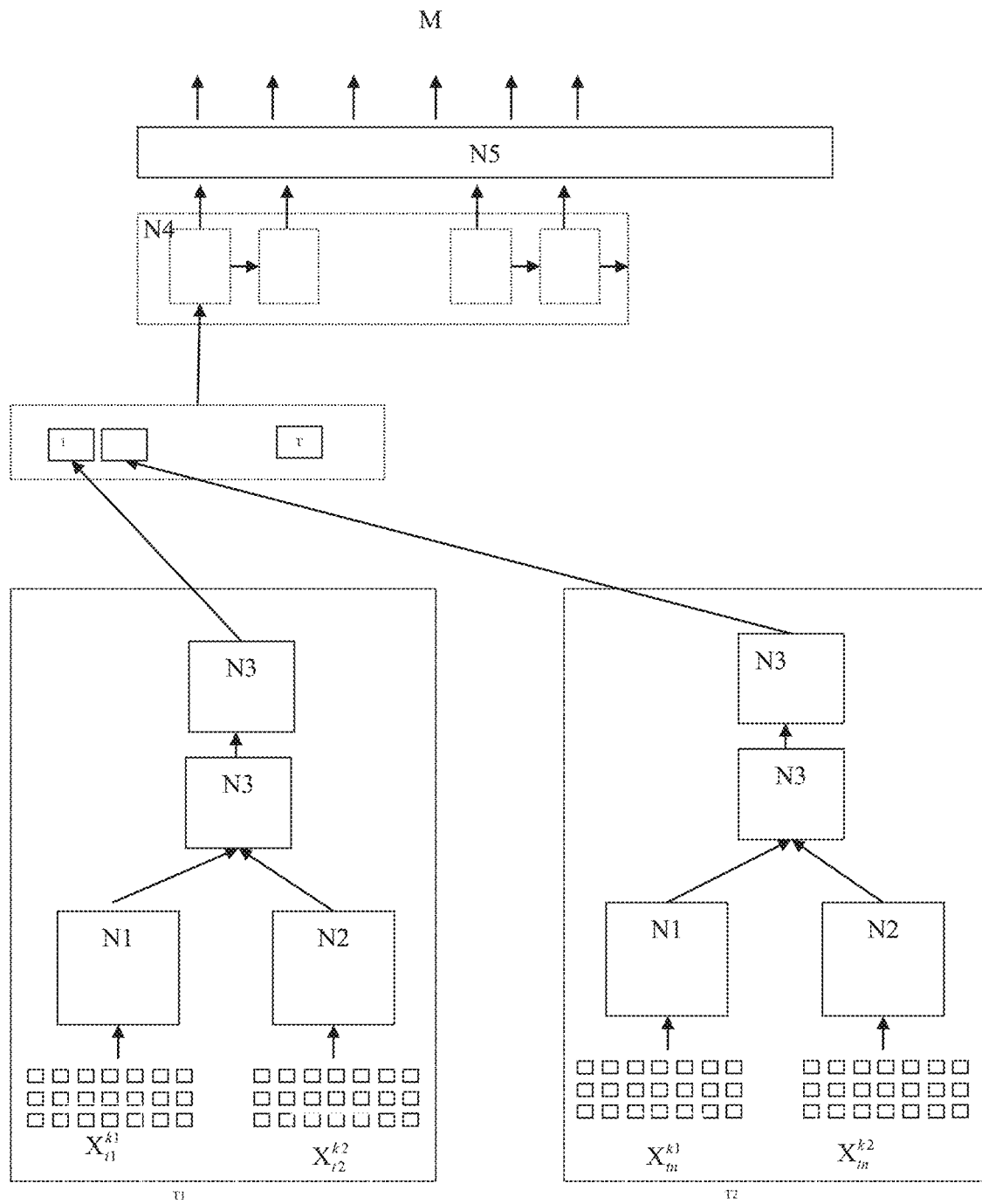
FIG. 2 is a schematic diagram of a specific example of a neural network architecture according to an embodiment of the present disclosure.

In an optional implementation, a relatively integrated neural network structure is designed according to some embodiments of the present disclosure. With this relatively integrated neural network structure, the data collected by the sensors is input into the neural network to calculate a transformation matrix M of a current image. The neural network in this embodiment of the present disclosure includes a convolutional neural network, a recursive neural network, and a fully connected network. To be specific, the neural network is divided into three parts, a first part is the convolutional neural network (CNN), a second part is the recursive neural network (RNN), and a third part is the fully connected network (namely, a regression network) used to calculate a final output result: the transformation matrix M. As shown in FIG. 2, an output of the convolutional neural network (CNN) is used as an input of the recursive neural network N4, an output of the recursive neural network N4 is used as an input of the fully connected network N5, and the final transformation matrix M is calculated by using the fully connected network N5.

Further optionally, there are multiple sensors, and the sensors may include an accelerometer and a gyroscope. The convolutional neural network includes a first convolutional neural network N3 and multiple second convolutional neural networks (N1 and N2) in one-to-one correspondence to the multiple sensors. An input of the first convolutional neural network is connected to outputs of the multiple second convolutional neural networks.

The foregoing optional implementations and further optional implementations all refer to a possible implementation of the technical solution of the present disclosure. The technical solution of the present disclosure may be implemented by using the foregoing implementations, or may be implemented in another manner. A specific implementation is not limited in the present disclosure.

Certainly, in this embodiment of the present disclosure, the sensors may further include another sensor that can detect movement of the probe, for example, a speed sensor. The second convolutional neural networks are in one-to-one correspondence to the sensors, and the first convolutional neural network may be used to merge data output by the multiple second convolutional neural networks, and perform deep learning and feature recognition on the merged data. The first convolutional neural network and the second convolutional neural networks in this embodiment of the present disclosure may be alternatively referred to as a convolutional layer. Multiple levels of neural networks are disposed to train, learn, and calculate the transformation matrix, and especially, convolutional neural networks are set to be in one-to-one correspondence to the sensors, so that the neural network can learn more precise feature information, thereby increasing transformation matrix calculation accuracy.

In this embodiment of the present disclosure, since the data collected by the probe in a moving process is continuous, for example, detection data of T duration, preprocessing needs to be performed, so that the data can meet the requirement of the neural network for processing and calculation. In this embodiment of the present disclosure, the step of obtaining motion data detected by the sensors includes: detection data, of to-be-detected duration, detected by each sensor is obtained; each piece of detection data is equally divided into multiple segments of data according to a dimension of the to-be-detected duration; and Fourier transform is performed on the multiple segments of data corresponding to each sensor, to obtain the motion data.

Specifically, the number of sensor types is set to K. If taking two types of sensors, namely, the accelerometer and the gyroscope, as an example, then K=2. Data generated by the two types of sensors is X. Each of the two sensors collects detection data of T duration (from 1 to T), and then, the detection data is equally divided into n segments of data, wherein an nth segment of data is $X_{tn}^k$. For $X_{tn}^k$, the dimension is D×U, wherein D is the number of dimensions of sensor data, and generally is three. Therefore, D=3. U is a length of one segment of data. For example, N pieces of data are collected in a direction x in duration T, and are equally divided into n segments of data. Therefore, U=N/n. For the data $X_{tn}^k$, Fourier transform is performed on data in each dimension, and fast Fourier transform (fast Fourier transform, FFT for short) may be performed, to obtain corresponding frequency domain data $A_{tn}^k$. The dimension of is $A_{tn}^k$ and a total data amount is D*F*n, wherein F=2*f, f refers to f main frequencies of current data, 2 represents a coefficient of the main frequencies, and the coefficient of the main frequencies includes a real number part and an imaginary number part corresponding to a sinusoidal component and a cosine component. As shown in FIG. 2, the collected data is preprocessed based on a sensor type and a time, and then is input into the corresponding convolutional neural networks based on groups, wherein k1 represents a first sensor, and k2 represents a second sensor.

In this embodiment of the present disclosure, processing such as segmentation and Fourier transform is performed on the data detected by the sensors, so that the data meets a calculation and recognition requirement of the neural network, and recognition and calculation can be performed for a sensor of any data type, thereby improving applicability of the neural network and calculation and recognition precision of the neural network.

The foregoing optional implementations and further optional implementations all refer to a possible implementation of the technical solution of the present disclosure. The technical solution of the present disclosure may be implemented by using the foregoing implementations, or may be implemented in another manner. A specific implementation is not limited in the present disclosure.

Further, in the foregoing step S102, the step of inputting the motion data into a pre-trained neural network, and calculating matrix parameters by using the neural network includes:

S1021: convolution calculation is performed on the motion data by using the convolutional neural network, to obtain a data feature of the motion data as an output of the convolutional neural network.

The convolutional neural network is mainly used to learn and recognize a feature of the motion data. The data feature of the motion data detected by the sensors and a data feature between different sensors are learnt by convolution calculation, and then the data features are output to the recursive neural network for recursive operation.

S1022: recursive operation is performed on the data features output by the convolutional neural network by using the recursive neural network, to obtain a recursive calculation result as an output of the recursive neural network.

S1023: regression calculation is performed on the recursive calculation result output by the recursive neural network by using the fully connected network, to obtain the matrix parameters.

According to this embodiment of the present disclosure, the convolutional neural network is used to train and learn the motion data to obtain the feature of the data detected by the sensors and a relationship between data of different sensors. Then, the recursive neural network is used to connect output results of the convolutional neural network in a time sequence, and then perform the recursive operation. Finally, the matrix parameters of the transformation matrix are obtained through regression by using the fully connected network.

As an optional implementation, when multiple neural network layers are used as the convolutional neural network, the step of performing convolution calculation on the motion data by using the convolutional neural network, to obtain a data feature of the motion data includes:

S11: convolution processing is performed on the motion data detected by the sensors corresponding to the second convolutional neural networks by using the second convolutional neural network.

Figure 3:
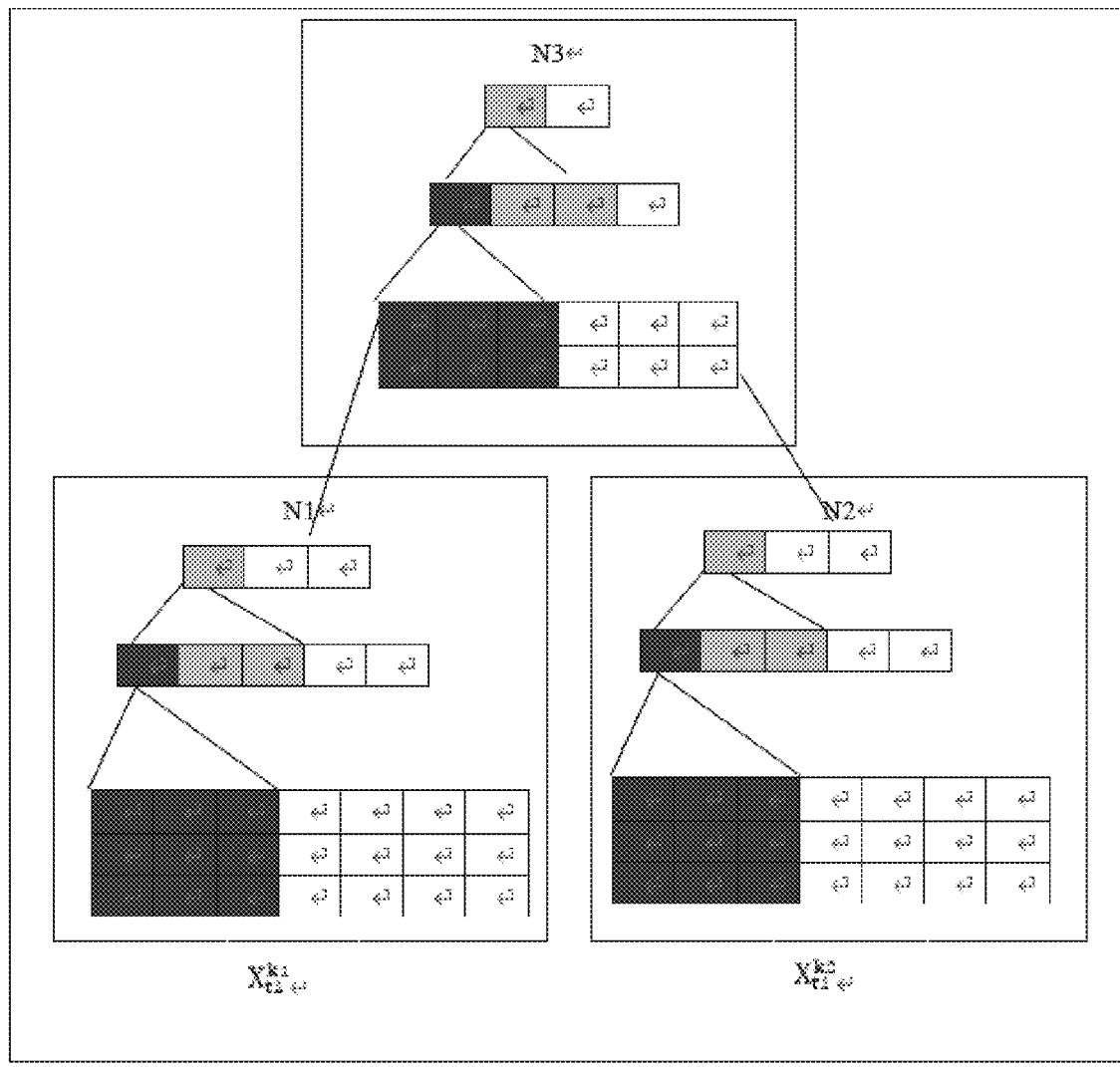
FIG. 3 is a schematic diagram of a specific example of a convolutional neural network according to an embodiment of the present disclosure.

In this embodiment of the present disclosure, there are multiple second convolutional neural networks, for example, N1 and N2 in FIG. 2 and FIG. 3. The second convolutional neural networks are independent of each other. Since each second convolutional neural network corresponds to one sensor, each second convolutional neural network needs to only process the data detected by the corresponding sensor.

Two sensors are used as an example for description. The sensors are respectively an accelerometer and a gyroscope. Since the accelerometer and the gyroscope are two different types of sensors, two neural networks, N1 and N2, with independent weights are used during training. N1 and N2 are independent of each other but have a same structure. N1 is used to train and learn sensor data of the accelerometer, and N2 is used to train and learn sensor data of the gyroscope. Specifically, in a training process, the data detected by the accelerometer is input into the convolutional neural network N1 for convolution processing, and the data detected by the gyroscope is input into the convolutional neural network N2 for convolution processing. As shown in FIG. 3, for two second convolutional neural networks, N1 and N2, with the same structure, the N1 and the N2 are trained to learn data features of different sensor data. Since the accelerometer and the gyroscope are sensors of two different types, the sensor data need to be trained by using two neural networks with independent weights, and correspondingly, a case is the same in a process of using the neural network. As described in the foregoing embodiment, the dimension input into the second convolutional neural network is D*F, a size of a convolution kernel of a first layer in convolutional layers corresponding to the second convolutional neural network is $k_w^{1}$*3, and sizes of convolution kernels of the following several layers of the second convolutional neural network (the neural network includes multiple convolutional layers) are all 1*3, wherein $k_q^{1}$ is equal to D, and is 3 in this embodiment of the present disclosure. The convolution kernel of the first layer is used to learn a relation between data of different dimensions of a single sensor. The convolution kernels of the subsequent layers are used to learn a relationship between deeper (depth) data.

S12: outputs of the multiple second convolutional neural networks are merged and convolution processing is performed by using the first convolutional neural network, to obtain the data feature.

As shown in FIG. 2 and FIG. 3, the first convolutional neural network N3 is used to merge data that is output by the second convolutional neural networks N1 and N2 after the second convolutional neural networks process the motion data of the multiple sensors, and perform convolution calculation processing on the merged result, to obtain a deeper data feature between the motion data detected by the multiple sensors and use the deeper data feature as an output result of the entire convolutional neural network for subsequent processing of the recursive neural network.

Optionally, the step of merging outputs of the multiple second convolutional neural networks and performing convolution processing by using the first convolutional neural network, to obtain the data feature includes: the data output by each second convolutional neural network is tiled into one-dimensional data, the one-dimensional data corresponding to the second convolutional neural networks is superposed, and deep convolution calculation is performed on the superposed data by using the first convolutional neural network, to obtain the data feature.

The foregoing optional implementation and further optional implementation all refer to a possible implementation of the technical solution of the present disclosure. The technical solution of the present disclosure may be implemented by using the foregoing implementation, or may be implemented in another manner. A specific implementation is not limited in the present disclosure.

As shown in FIG. 3, the first convolutional neural network N3 is used to tile the data that formed by the convolutional neural networks N1 and N2 by processing the multiple sensor data, into one-dimensional data, superpose the one-dimensional data, and then perform deep learning and processing. The first convolutional neural network includes multiple convolutional layers. A size of a convolution kernel of the first layer is $k_w^{2}$*3, and sizes of the convolution kernels of subsequent several layers of the neural network are all 1*3, wherein $k_w^{1}$ is K, which is equal to the number of sensors, that is 2. The convolutional neural network N3 is used to merge data of the two sensors and learn a deeper feature thereof.

In this embodiment of the present disclosure, each of the first convolutional neural network N3 and the second convolutional neural networks N1 and N2 is constructed by using multiple convolutional layers, and is provided with an activation function and a normalization layer. The activation function may be a relu rectified linear activation function, and the normalization layer may be a batch normalization layer, to ensure that an average and a variance of an input are fixed in a particular range, therefore the training precision is improved.

It should be noted that the number of sensors and the data of the neural network described in the foregoing embodiments are merely to describe the technical solution of the application more clearly. As can be learned from the principles described above, for a case of using three sensors or more sensors, only small adjustments need to be made on the solution, and the case also belongs to the protection scope of the present disclosure.

In this embodiment of the present disclosure, data output by the first convolutional neural network, that is an input of the recursive neural network, is the data feature learned by using the data collected by the sensors in a chronological order in a time period. In a conventional method for calculating a relative displacement based on data of a sensor such as the accelerometer, the integral of acceleration is calculated in a small time period, to obtain a speed, and then, the integral of the speed is calculated to obtain the displacement. The input in this process is data collected in unit time. The recursive neural network in this embodiment of the present disclosure is also based on a similar principle, and can learn summation integration features from an earlier level, to calculate a final output result from another perspective.

Figure 4:
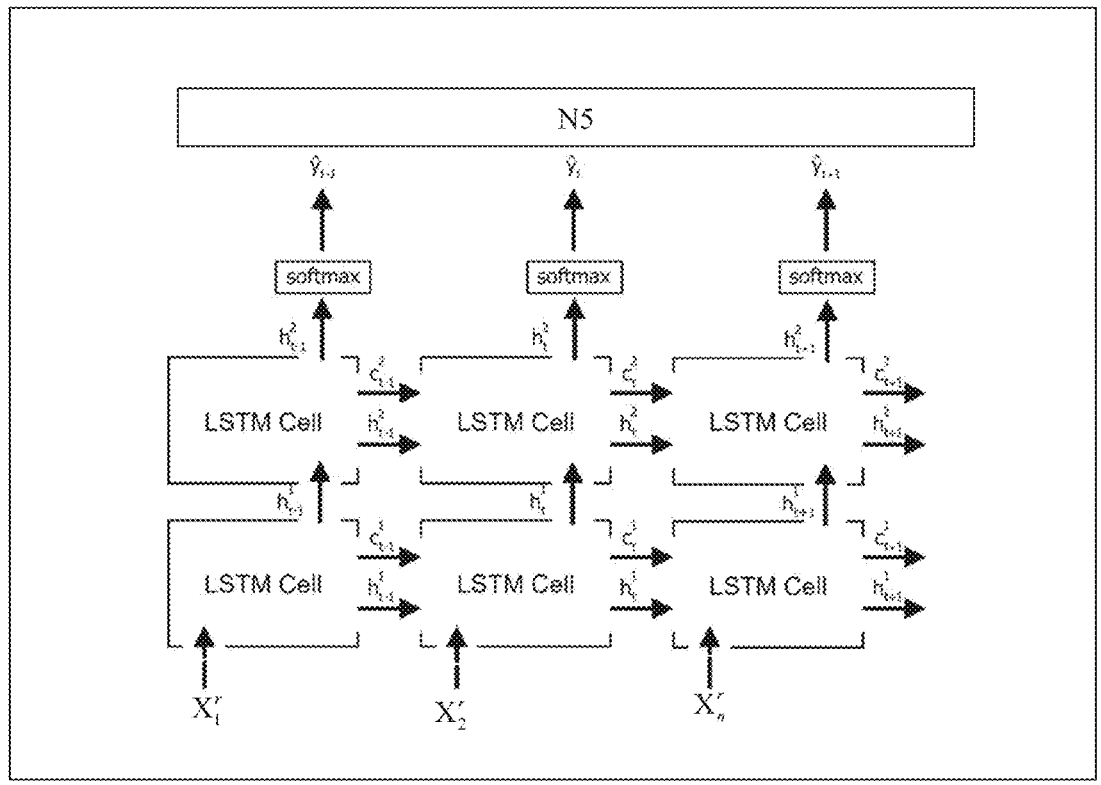
FIG. 4 is a schematic diagram of a specific example of a recursive neural network according to an embodiment of the present disclosure.

Specifically, the foregoing content is used as an example, the motion data detected by the sensors is sent to the convolutional neural networks N1 and N2 in a chronological order and based on sensor types, and an output is $X_t^r$, wherein t=1, . . . , n, respectively representing output results of the neural networks N1, N2, and N3 after the neural networks by processing the sensor inputs in multiple time periods. The output results are connected in a chronological order as an input of the recursive neural network N4. The recursive neural network in this embodiment of the present disclosure may be obtained by stacking multiple LSTM network layers, and specifically, two layers may be stacked. An optional recursive neural network structure is shown in FIG. 4. An output of the recursive neural network layer in each stage is sent to the fully connected network N5. The fully connected network N5 is used to perform regression operation to obtain the final matrix parameters of the transformation matrix of the probe during movement. A form of the transformation matrix of the probe during movement is:

$$M = \begin{vmatrix} \cos\theta & \sin\theta & \Delta x \\ -\sin\theta & \cos\theta & \Delta y \\ 0 & 0 & 1 \end{vmatrix}.$$

Therefore, the parameters that need to be obtained through training and learning are a rotation angle θ of the probe, and offsets Δx and Δy of the probe. The calculated result is used as the parameters of the transformation matrix of the images for final image transformation and stitching. The transformation matrix is obtained through summarization and derivation based on a relative relationship between movement images.

The foregoing optional implementation and a further optional implementation both refer to a possible implementation of the technical solution of the present disclosure. The technical solution of the present disclosure may be implemented by using the foregoing implementations, or may be implemented in another manner. A specific implementation is not limited in the present disclosure.

Figure 5:
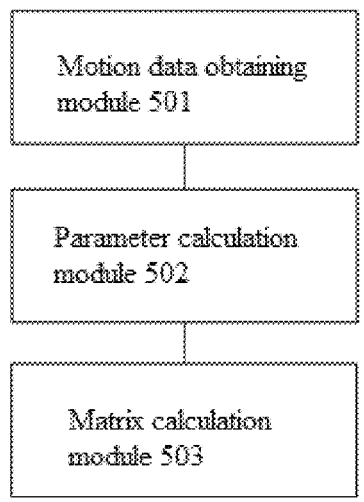
FIG. 5 is a principle block diagram of a specific example of a transformation matrix obtaining apparatus according to Embodiment 1 of the present disclosure.

In another aspect, the embodiment of the present disclosure further provides a transformation matrix obtaining apparatus. The apparatus can be used to perform the transformation matrix obtaining method in the foregoing embodiment. As shown in FIG. 5, the apparatus includes:

a motion data obtaining module 501, configured to obtain motion data detected by sensors, wherein the sensors are disposed on a probe used to collect images, and the motion data is used to represent a moving trend of the probe during image collection;

a parameter calculation module 502, configured to input the motion data into a pre-trained neural network, and calculate matrix parameters by using the neural network; and a matrix calculation module 503, configured to calculate a transformation matrix by using the matrix parameters, wherein the transformation matrix is used to stitch the images collected by the probe, to obtain a panoramic image.

According to this embodiment of the present disclosure, the motion data of the images collected by the probe is obtained, and the motion data is calculated and analyzed by using the pre-trained neural network, to obtain a moving change of the probe, and calculate the transformation matrix of the images. To be specific, an image change is calculated indirectly, and the transformation matrix can be calculated and the images can be stitched without using features of the images. Factors such as brightness and features of the images do not impose any impact, thereby improving transformation matrix calculation accuracy, and improving an image stitching effect.

The transformation matrix obtaining apparatus in this embodiment of the present disclosure corresponds to the transformation matrix obtaining method in the foregoing embodiment. For specific descriptions, refer to the foregoing embodiment, and details are not described herein again.

Embodiment 2

Figure 6:
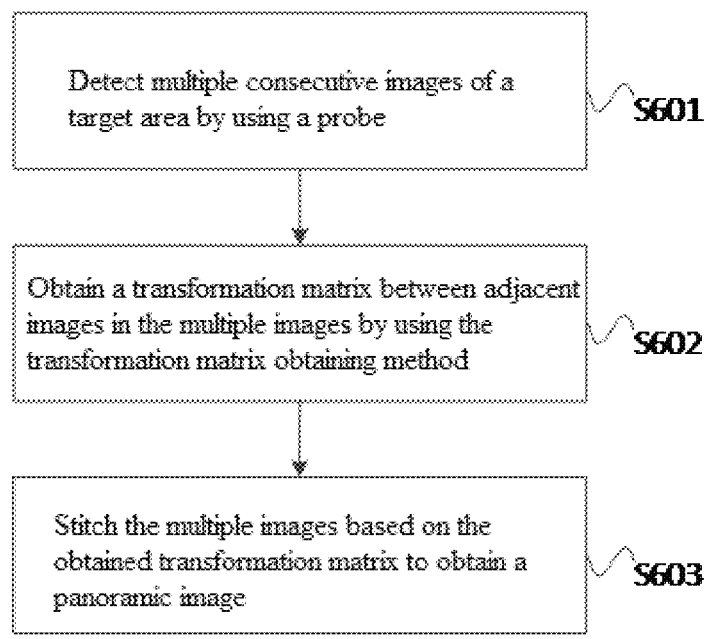
FIG. 6 is a flowchart of a specific example of a panoramic image stitching method according to Embodiment 2 of the present disclosure.

This embodiment of the present disclosure provides a panoramic image stitching method. The method is mainly used to stitch two or more overlapping images to form a panoramic image. As shown in FIG. 6, the method includes the following steps:

Step S601, multiple consecutive images of a target area are detected by using a probe.

As described in Embodiment 1, the probe is provided with sensors used to detect motion data of the probe, and the probe needs to be moved in an image capturing process, to capture all the target area. The multiple images are continuous mainly because images (such as video images) are continuous in a detection process of the probe.

Step S602, a transformation matrix between adjacent images in the multiple images is obtained by using the transformation matrix obtaining method.

The transformation matrix obtaining method in this embodiment of the present disclosure is also the transformation matrix obtaining method described in the foregoing Embodiment 1. For specific working principles and details, refer to the foregoing embodiment, and details are not described herein again.

Step S603, the multiple images are stitched based on the obtained transformation matrix to obtain a panoramic image.

Figure 7:
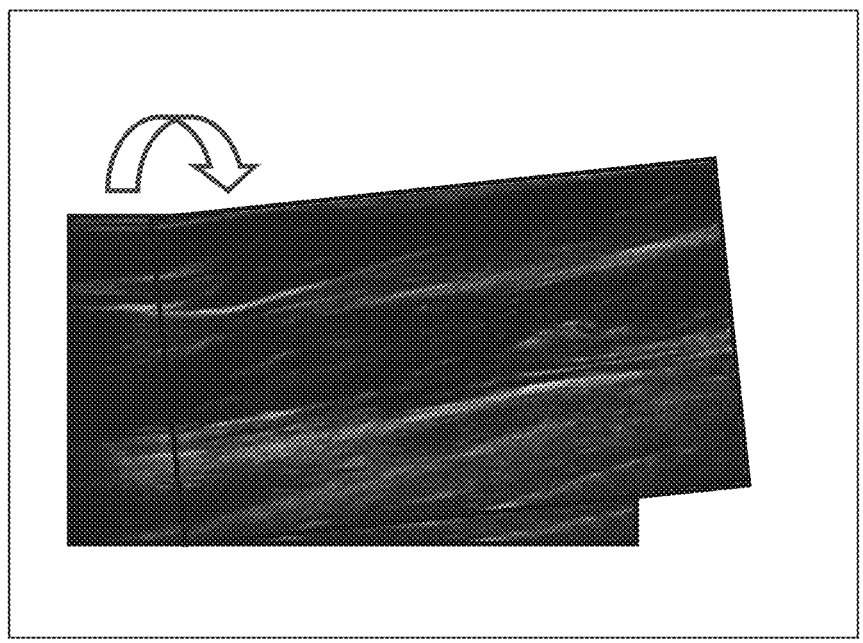
FIG. 7 is a schematic diagram of a specific example of image stitching according to an embodiment of the present disclosure.

In this embodiment of the present disclosure, the transformation matrix between the images is obtained by using the transformation matrix obtaining method and based on the motion data detected by the sensors, and the detected multiple images can be stitched to obtain the panoramic image. An example of image stitching is shown in FIG. 7, and an image A and an image B are stitched together. Since the transformation matrix can be obtained without using features of the images, the transformation matrix can be calculated and the images can be stitched, and factors such as brightness and features of the images do not impose any impact, thereby improving transformation matrix calculation accuracy, and improving an image stitching effect.

Figure 8:
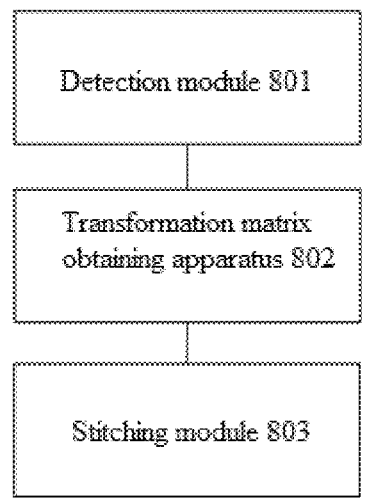
FIG. 8 is a principle block diagram of a specific example of a panoramic image stitching apparatus according to Embodiment 2 of the present disclosure.

In another aspect, this embodiment of the present disclosure further provides a panoramic image stitching apparatus. The apparatus may be configured to perform the panoramic image stitching method in the foregoing embodiment. As shown in FIG. 8, the apparatus includes:

a detection module 801, configured to detect multiple consecutive images of a target area by using a probe;

a transformation matrix obtaining apparatus 802, configured to obtain a transformation matrix between adjacent images in the multiple images, wherein the transformation matrix obtaining apparatus 802 is the apparatus in FIG. 5 in Embodiment 1, and for details, refer to the foregoing descriptions; and a stitching module 803, configured to stitch the multiple images based on the obtained transformation matrix to obtain a panoramic image.

In this embodiment of the present disclosure, the transformation matrix between the images is obtained by using the transformation matrix obtaining method and based on the motion data detected by the sensors, and the detected multiple images can be stitched to obtain the panoramic image. The transformation matrix can be obtained without using features of the images, the transformation matrix can be calculated and the images can be stitched, and factors such as brightness and features of the images do not impose any impact, thereby improving transformation matrix calculation accuracy, and improving an image stitching effect.

The panoramic image stitching apparatus in this embodiment of the present disclosure corresponds to the panoramic image stitching method in the foregoing embodiment. For specific descriptions, refer to the foregoing embodiment, and details are not described herein again.

Embodiment 3

Figure 9:
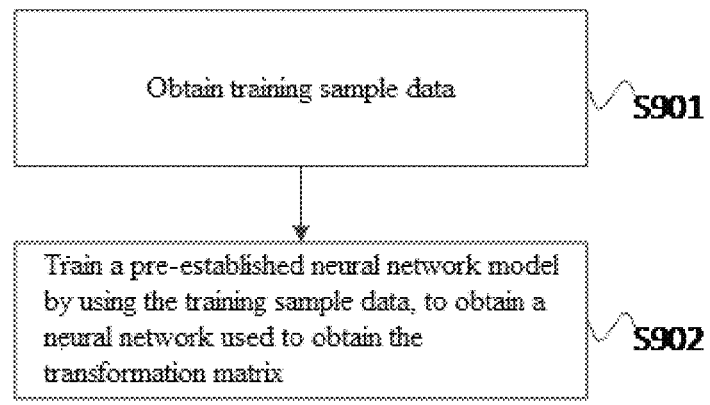
FIG. 9 is a flowchart of a specific example of a neural network training method according to Embodiment 3 of the present disclosure.

This embodiment of the present disclosure also provides a neural network training method. The training method is mainly used to train the neural network described in the foregoing Embodiment 1. As shown in FIG. 9, the method includes the following steps:

Step S901, training sample data is obtained, wherein the sample data includes: motion data detected by sensors and matrix parameters corresponding to the motion data, the sensors are disposed on a probe used to collect images, the motion data is used to represent a moving trend of the probe during image collection, and the matrix parameters are parameters in a transformation matrix used to obtain a panoramic image through stitching.

In this embodiment of the present disclosure, the motion data and the annotated matrix parameters are used as the training sample data. The training sample data may be divided into a training set and a test set. The data mainly includes the motion data and the annotated corresponding matrix parameters, for the training of a neural network model.

Figure 10:
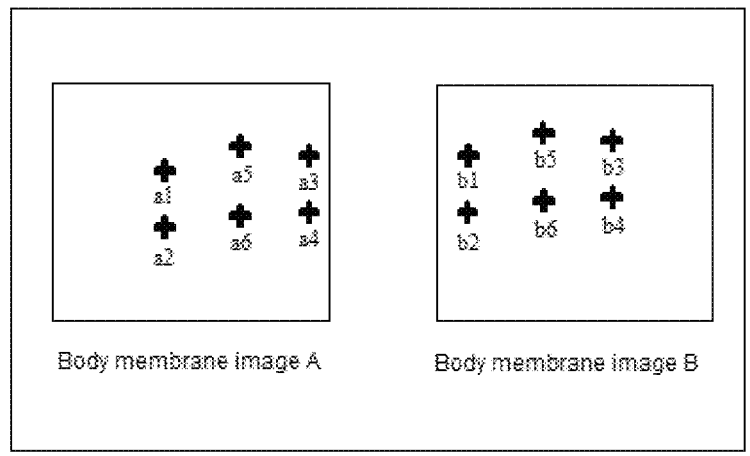
FIG. 10 is a schematic diagram of a specific example of body membrane images according to Embodiment 3 of the present disclosure.

In this embodiment of the present disclosure, the accurate matrix parameters need to be annotated, that is, the accurate transformation matrix is annotated, so that precision of a training result can meet a requirement. Since the transformation matrix cannot be directly obtained from two images, a body membrane image is used for training in this embodiment of the present disclosure. The body membrane image features in that a fixed target site can be disposed inside a body membrane. In a process of moving the probe, the target site can be clearly seen in a scanned image of the body membrane, as shown in FIG. 10. Locations of a same target site in the two images may be determined to calculate the transformation matrix. Advantages of the body membrane image lie in that the image is clear, and the calculated transformation matrix is reliable and correct.

To be specific, the step of obtaining training sample data includes: body membrane images collected by the probe are obtained; a transformation matrix of two adjacent body membrane images is determined by using coordinates of target sites disposed on the adjacent body membrane images; matrix parameters of the transformation matrix are calculated by using a least square method; and the motion data detected by the sensors are obtained, and the matrix parameters and the motion data are used as the training sample data.

Specifically, assuming that coordinates of a target site in an A image are Pa(x, y){1 . . . n}, coordinates, Pb(x, y){1 . . . n}, of the target site in a B image can be obtained based on the image, and $$P^b_{(x',y')} = M * P^a_{(x,y)} = \begin{vmatrix} \cos\theta & \sin\theta & \Delta x \\ -\sin\theta & \cos\theta & \Delta y \\ 0 & 0 & 1 \end{vmatrix} * P^a_{(x,y)},$$

wherein * represents matrix multiplication.

The following is obtained by minimizing an error between an actual value and a calculated value by using the least square method:

$$E = \sum_1^n \{[x'_i - \Delta x - (x_i\cos\theta - y_i\sin\theta)]^2 + [y'_i - \Delta y - (x_i\sin\theta + y_i\cos\theta)]^2\},$$

wherein $(x_i, y_i)$ and $(x_i', y_i')$ are coordinates of a corresponding target site in the A image and the B image, a value E is minimized, and a corresponding derivative is calculated as 0:

$$\frac{\partial E}{\partial \theta} = 0; \frac{\partial E}{\partial \Delta x} = 0; \text{ and } \frac{\partial E}{\partial \Delta y} = 0.$$

Optimal matrix parameters θ, Δx, and Δy can be calculated, to obtain the corresponding transformation matrix M.

Step S902, a pre-established neural network model is trained by using the training sample data, to obtain a neural network that used to obtain the transformation matrix.

In a process of moving the probe, sensor data in a fixed time interval is collected, a transformation matrix M of image moving and transformation in the current interval is calculated, the data is input into the neural network for training, to iteratively calculate optimal network parameters.

In this embodiment of the present disclosure, the neural network model is trained by using the motion data detected by the sensors and the matrix parameters, so that the neural network model can learn and recognize a data relationship between the motion data and the matrix parameters The neural network is obtained and subsequently used to recognize a corresponding transformation matrix for other motion data. An image change is indirectly calculated by analyzing a movement change of the probe by using the neural network, thereby improving accuracy.

Another aspect of the embodiments of the present disclosure further provides a neural network training apparatus.

Figure 11:
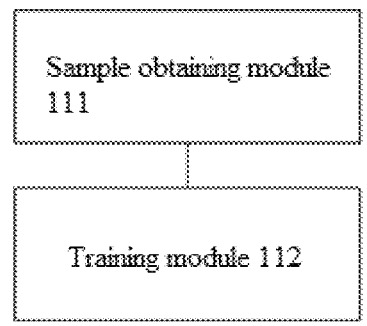
FIG. 11 is a principle block diagram of a specific example of a neural network training apparatus according to Embodiment 3 of the present disclosure.

The apparatus may be configured to perform the foregoing neural network training method. As shown in FIG. 11, the apparatus includes:

a sample obtaining module 111, configured to obtain training sample data, wherein the sample data includes motion data detected by sensors and matrix parameters corresponding to the motion data, the sensors are disposed on a probe used to collect images, the motion data is used to represent a moving trend of the probe during image collection, and the matrix parameters are parameters in a transformation matrix used to obtain a panoramic image through stitching; and a training module 112, configured to train a pre-established neural network model by using the training sample data to obtain a neural network that used to obtain the transformation matrix.

In this embodiment of the present disclosure, the neural network model is trained by using the motion data detected by the sensors and the matrix parameters, so that the neural network model can learn and recognize a data relationship between the motion data and the matrix parameters. The neural network is obtained and subsequently used to recognize a corresponding transformation matrix for other motion data. An image change is indirectly calculated by analyzing a movement change of the probe by using the neural network, thereby improving accuracy.

The neural network training apparatus in this embodiment of the present disclosure corresponds to the neural network training method in the foregoing embodiment. For specific descriptions, refer to the foregoing embodiment, and details are not described herein again.

Embodiment 4

Figure 12:
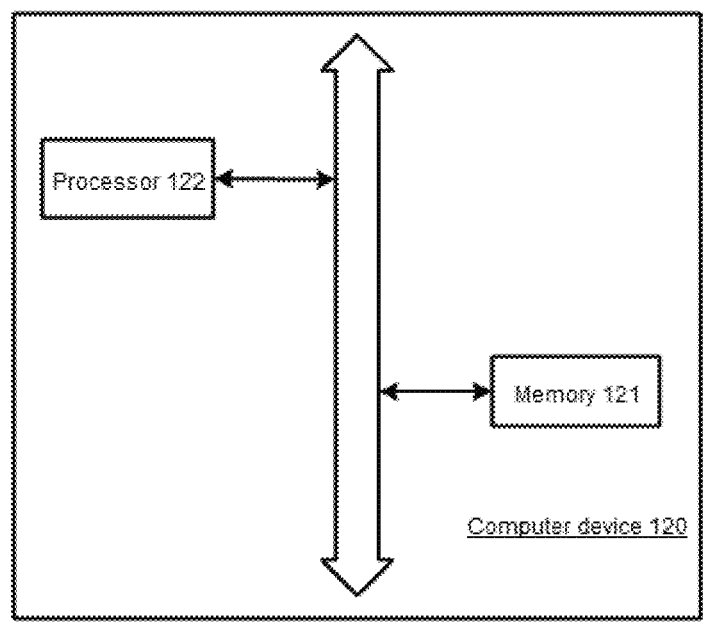
FIG. 12 is a schematic diagram of a hardware structure of a computer apparatus according to an embodiment of the present disclosure.

This embodiment further provides a computer apparatus, for example, a desktop computer, a rack server, a blade server, a tower server, or a cabinet server (including an independent server, or a server cluster that includes multiple servers) that can execute a program. The computer apparatus 120 in this embodiment at least includes, but not limited to: a memory 121 and a processor 122 that can be in communication connection to each other by using a system bus, as shown in FIG. 12. It should be pointed out that FIG. 12 shows only a computer apparatus 120 including components 121 and 122, but it should be understood that it is not required to implement all shown components, and more or fewer components may be implemented instead.

In this embodiment, the memory 121 (namely, a readable storage medium) includes a flash memory, a hard disk, a multimedia card, a card-type memory (for example, an SD or DX memory), a random access memory (RAM), a static random access memory (SRAM), a read-only memory (ROM), an electrically erasable programmable read-only memory (EEPROM), a programmable read-only memory (PROM), a magnetic memory, a magnetic disk, an optical disc, and the like. In some embodiments, the memory 121 may be an internal storage unit of the computer apparatus 120, for example, a hard disk or an internal memory of the computer apparatus 120. In some other embodiments, the memory 121 may be alternatively an external storage device of the computer apparatus 120, for example, a plug-in hard disk, a smart media card (SMC), a secure digital (SD) card, a flash card, and the like. Certainly, the memory 121 may alternatively include both an internal storage unit of the computer apparatus 120 and an external storage device thereof. In this embodiment, the memory 21 generally is configured to store an operating system and various application software installed in the computer apparatus 120, for example, program codes of transformation matrix obtaining, panoramic image stitching, and neural network training methods in the embodiments. In addition, the memory 121 may also be used to temporarily store various types of data that have been output or will be output.

In some embodiments, the processor 122 may be a central processing unit (CPU), a controller, a microcontroller, a microprocessor, or other data processing chips. Generally, the processor 122 is configured to control an overall operation of the computer apparatus 120. In this embodiment, the processor 122 is configured to run the program codes or process data stored in the memory 121, for example, implement transformation matrix obtaining, panoramic image stitching, and neural network training methods of the embodiments.

This embodiment further provides a computer-readable storage medium, for example, a flash memory, a hard disk, a multimedia card, a card-type memory (for example, an SD or DX memory), a random access memory (RAM), a static random access memory (SRAM), a read-only memory (ROM), an electrically erasable programmable read-only memory (EEPROM), a programmable read-only memory (PROM), a magnetic memory, a magnetic disk, an optical disc, a server, or an App application mall. The computer storage medium stores a computer program. When the program is executed by a processor, a corresponding function is implemented. The computer-readable storage medium in this embodiment is configured to store transformation matrix obtaining apparatus, panoramic image stitching apparatus, and neural network training apparatuses, and when the apparatuses are executed by a processor, methods for transformation matrix obtaining, panoramic image stitching, and neural network training in the embodiments are implemented.

Obviously, the foregoing embodiments are merely examples for clear description, but are not intended to limit the implementation. A person of ordinary skill in the art may make other changes or modifications in different forms based on the foregoing descriptions. It is unnecessary and impossible to list all implementation methods herein. The obvious changes or modifications derived therefrom still fall within the protection scope of the present disclosure.

The invention claimed is:

1. A transformation matrix obtaining method, comprising the following steps:
    obtaining motion data detected by sensors, wherein the sensors are disposed on a probe used to collect images, and the motion data is used to represent a moving trend of the probe during image collection;
    inputting the motion data into a pre-trained neural network, and calculating matrix parameters by using the neural network; and
    calculating a transformation matrix by using the matrix parameters, wherein the transformation matrix is used to stitch images collected by the probe, to obtain a panoramic image.

2. The transformation matrix obtaining method according to claim 1, wherein the neural network comprises a convolutional neural network, a recursive neural network, and a fully connected network, and the step of inputting the motion data into a pre-trained neural network, and calculating matrix parameters by using the neural network comprises:
    performing, by using the convolutional neural network, convolution calculation on the motion data, to obtain a data feature of the motion data as an output of the convolutional neural network;
    performing, by using the recursive neural network, recursive operation on the data feature output by the convolutional neural network, to obtain a recursive calculation result as an output of the recursive neural network; and
    performing, by using the fully connected network, regression calculation on the recursive calculation result output by the recursive neural network, to obtain the matrix parameters.

3. The transformation matrix obtaining method according to claim 2, wherein there are multiple sensors, and the convolutional neural network comprises a first convolutional neural network and multiple second convolutional neural networks in one-to-one correspondence to the multiple sensors, wherein an input of the first convolutional neural network is connected to outputs of the multiple second convolutional neural networks.

4. The transformation matrix obtaining method according to claim 3, wherein the sensors comprise an accelerometer and a gyroscope.

5. The transformation matrix obtaining method according to claim 3, wherein the step of performing convolution calculation on the motion data by using the convolutional neural network, to obtain a data feature of the motion data comprises:
    performing, by using the second convolutional neural networks, convolution processing on the motion data detected by the sensors corresponding to the second convolutional neural networks; and
    merging outputs of the multiple second convolutional neural networks and performing convolution processing by using the first convolutional neural network, to obtain the data feature.

6. The transformation matrix obtaining method according to claim 5, wherein the step of merging outputs of the multiple second convolutional neural networks and performing convolution processing by using the first convolutional neural network, to obtain the data feature comprises:
    tiling data output by each second convolutional neural network into one-dimensional data; and
    superposing the one-dimensional data corresponding to all of the second convolutional neural networks, and performing deep convolution calculation on the superposed one-dimensional data by using the first convolutional neural network, to obtain the data feature.

7. The transformation matrix obtaining method according to claim 5, wherein the step of obtaining motion data detected by sensors comprises:
    obtaining detection data, of to-be-detected duration, detected by each sensor;
    equally dividing each piece of detection data into multiple segments of data according to a dimension of the to-be-detected duration; and
    performing Fourier transform on the multiple segments of data corresponding to each sensor to obtain the motion data.

8. A panoramic image stitching method, comprising the following steps:
    detecting consecutive multiple images of a target area by using a probe;
    obtaining a transformation matrix between adjacent images in the multiple images by using the transformation matrix obtaining method according to claim 1; and stitching the multiple images based on the obtained transformation matrix to obtain a panoramic image.

9. A neural network training method, comprising the following steps:
obtaining training sample data, wherein the sample data comprises motion data detected by sensors and matrix parameters corresponding to the motion data, the sensors are disposed on a probe used to collect images, the motion data is used to represent a moving trend of the probe during image collection, and the matrix parameters are parameters in a transformation matrix used to obtain a panoramic image through stitching; and
training a pre-established neural network model by using the training sample data, to obtain a neural network used to obtain the transformation matrix.

10. The neural network training method according to claim 9, wherein the step of obtaining training sample data comprises:
obtaining body membrane images collected by the probe;
determining a transformation matrix of two adjacent body membrane images by using coordinates of target sites disposed on the adjacent body membrane images;
calculating matrix parameters of the transformation matrix by using a least square method; and
obtaining the motion data detected by the sensors, and using the matrix parameters and the motion data as the training sample data.

11. A computer apparatus, comprising a memory, a processor, and a computer program that is stored in the memory and that can be run on the processor, and when executing the computer program, the processor implements the steps of the method according to claim 1.

12. A non-transitory computer-readable storage medium, storing a computer program, wherein when the computer program is executed by a processor, the steps of the method according to claim 1 are implemented.

13. A computer apparatus, comprising a memory, a processor, and a computer program that is stored in the memory and that can be run on the processor, and when executing the computer program, the processor implements the steps of the method according to claim 9.

14. A non-transitory computer-readable storage medium, storing a computer program, wherein when the computer program is executed by a processor, the steps of the method according to claim 9 are implemented.

15. The transformation matrix obtaining method according to claim 4, wherein the step of performing convolution calculation on the motion data by using the convolutional neural network, to obtain a data feature of the motion data comprises:
performing, by using the second convolutional neural networks, convolution processing on the motion data detected by the sensors corresponding to the second convolutional neural networks; and
merging outputs of the multiple second convolutional neural networks and performing convolution processing by using the first convolutional neural network, to obtain the data feature.

16. An apparatus for obtaining transformation matrix, comprising:
a memory configured to store instructions; and
a processor coupled to the memory and configured to execute the instructions to cause the apparatus to perform:
obtaining motion data detected by sensors, wherein the sensors are disposed on a probe used to collect images, and the motion data is used to represent a moving trend of the probe during image collection;
inputting the motion data into a pre-trained neural network, and calculating matrix parameters by using the neural network; and
calculating a transformation matrix by using the matrix parameters, wherein the transformation matrix is used to stitch images collected by the probe, to obtain a panoramic image.

17. The apparatus of claim 16, wherein the neural network comprises a convolutional neural network, a recursive neural network, and a fully connected network, and wherein the processor is further configured to execute the instructions to cause the apparatus to perform:
performing, by using the convolutional neural network, convolution calculation on the motion data, to obtain a data feature of the motion data as an output of the convolutional neural network;
performing, by using the recursive neural network, recursive operation on the data feature output by the convolutional neural network, to obtain a recursive calculation result as an output of the recursive neural network; and
performing, by using the fully connected network, regression calculation on the recursive calculation result output by the recursive neural network, to obtain the matrix parameters.

18. The apparatus of claim 17, comprising multiple sensors, wherein the convolutional neural network comprises a first convolutional neural network and multiple second convolutional neural networks in one-to-one correspondence to the multiple sensors, further wherein an input of the first convolutional neural network is connected to outputs of the multiple second convolutional neural networks.

19. The apparatus of claim 18, wherein the processor is further configured to execute the instructions to cause the apparatus to perform:
performing, by using the second convolutional neural networks, convolution processing on the motion data detected by the sensors corresponding to the second convolutional neural networks; and
merging outputs of the multiple second convolutional neural networks and performing convolution processing by using the first convolutional neural network, to obtain the data feature.

20. The apparatus of claim 19, wherein the processor is further configured to execute the instructions to cause the apparatus to perform:
tiling data output by each second convolutional neural network into one-dimensional data; and
superposing the one-dimensional data corresponding to all of the second convolutional neural networks, and performing deep convolution calculation on the superposed one-dimensional data by using the first convolutional neural network, to obtain the data feature.

* * * * *